United States Patent
McCain

(10) Patent No.: US 11,857,008 B1
(45) Date of Patent: *Jan. 2, 2024

(54) GARMENTS FOR PEDIATRIC PATIENTS WITH POST-OPERATIVE DRAIN COMPARTMENTS

(71) Applicant: CREATE TO OVERCOME LLC, Kirkland, WA (US)

(72) Inventor: Aisha McCain, Pittsburg, CA (US)

(73) Assignee: Create To Overcome LLC, Pittsburg, CA (US)

( * ) Notice: Subject to any disclaimer, the term of this patent is extended or adjusted under 35 U.S.C. 154(b) by 617 days.

This patent is subject to a terminal disclaimer.

(21) Appl. No.: 16/260,057

(22) Filed: Jan. 28, 2019

Related U.S. Application Data

(63) Continuation-in-part of application No. 15/726,307, filed on Oct. 5, 2017, now Pat. No. 10,188,160.

(51) Int. Cl.
*A41D 13/12* (2006.01)
*A41D 27/20* (2006.01)

(52) U.S. Cl.
CPC ..... *A41D 13/1245* (2013.01); *A41D 13/1272* (2013.01); *A41D 27/20* (2013.01); *A41D 13/1281* (2013.01); *A61M 2209/088* (2013.01)

(58) Field of Classification Search
CPC ............ A41D 13/0012; A41D 13/1245; A41D 27/20; A41D 2400/32; A41D 13/1236;

(Continued)

(56) References Cited

U.S. PATENT DOCUMENTS

| 1,444,750 A | 2/1923 | Moore | 2/94 |
| 1,520,962 A | 12/1924 | North | 2/102 |

(Continued)

FOREIGN PATENT DOCUMENTS

| CN | 202653199 U | * | 1/2013 | |
| CN | 203762333 U | * | 8/2014 | |
| WO | WO-2020145963 A1 | * | 7/2020 | ......... A41D 13/0012 |

OTHER PUBLICATIONS

English translation of CN 202653199 (Liu H); Doc pub. Jan. 2013.*

*Primary Examiner* — Amy Vanatta
(74) *Attorney, Agent, or Firm* — Cynthia Lamon; Lamon Patent Services

(57) ABSTRACT

Garments with post-operative drain compartments along an interior of the garment are manufactured and provided to a pediatric (child or adolescent) patients after surgery. The garment has a first plurality of post-operative drain compartments on a first side of the garment and a second plurality of post-operative drain compartments on a second side of the garment. Each of the post-operative drain compartments supports a reservoir of a post-operative drain. After a surgical procedure involving post-operative drains as part of recovery, a child or adolescent wears the garment and inserts the reservoir of a post-operative drain into one of the post-operative drain compartments. The garment supports at least four post-operative drains. One of the post-operative drain compartments is disposed above another one of the post-operative drain compartments. Each of the openings post-operative drain compartments remains open and does not include any fastening mechanism.

11 Claims, 9 Drawing Sheets

FRONT PERSPECTIVE VIEW OF OPENING OF GARMENT HAVING POST-OPERATIVE DRAIN COMPARTMENTS WHEN WORN BY USER

(58) Field of Classification Search
CPC ........ A41D 13/1281; A41D 1/02; A41D 1/04;
A41D 1/002; A41D 1/22; A41D 13/1263;
A41D 27/204; A41D 13/1272; A41D
13/1254; A41D 13/12; A41D 13/1209;
A41D 27/205; A41D 13/0058; A41D
1/18; A41D 3/02; A61M 2209/088
USPC .......................... 2/194, 94, 114; D2/720, 839
See application file for complete search history.

(56) References Cited

U.S. PATENT DOCUMENTS

| | | | | |
|---|---|---|---|---|
| 3,055,133 | A | 9/1962 | Anderson | 40/586 |
| 5,142,702 | A | 9/1992 | Piloian | 40/586 |
| 5,278,998 | A * | 1/1994 | Book | A41D 13/0012 |
| | | | | 224/648 |
| D421,329 | S * | 3/2000 | Adams | D2/847 |
| 6,574,800 | B1 | 6/2003 | Leger et al. | A41D 1/22 |
| D509,343 | S * | 9/2005 | Bragg | A41D 27/24 |
| | | | | D2/840 |
| 7,396,272 | B1 | 7/2008 | Newlen | 450/54 |
| 7,823,221 | B2 | 11/2010 | Green | 2/114 |
| 8,105,371 | B1 * | 1/2012 | Giocondo, Jr. | A41D 1/04 |
| | | | | 607/108 |
| D657,939 | S * | 4/2012 | Mathews | D2/847 |
| D764,145 | S | 8/2016 | Mathews | D2/828 |
| D816,301 | S * | 5/2018 | Notarianni | D2/840 |
| 10,264,831 | B1 * | 4/2019 | Hemker | A41D 13/1245 |
| 2004/0172734 | A1 * | 9/2004 | Hartbrodt | A41D 13/02 |
| | | | | 2/97 |
| 2004/0226073 | A1 | 11/2004 | McCullar et al. | 2/114 |
| 2006/0156450 | A1 | 7/2006 | McGrath | 2/114 |
| 2006/0173427 | A1 * | 8/2006 | Urbina | A41D 13/1245 |
| | | | | 604/327 |
| 2006/0253954 | A1 | 11/2006 | Music | 2/115 |
| 2007/0113316 | A1 | 5/2007 | King | 2/102 |
| 2007/0271672 | A1 | 11/2007 | Lentini | 2/69 |
| 2008/0000006 | A1 | 1/2008 | Ochoa et al. | 2/114 |
| 2008/0184455 | A1 | 8/2008 | Blume | 2/114 |
| 2008/0312615 | A1 | 12/2008 | Hunter | 604/345 |
| 2010/0205720 | A1 | 8/2010 | Ortega Astor | 2/247 |
| 2011/0041229 | A1 * | 2/2011 | Niemi | A41D 19/01535 |
| | | | | 607/108 |
| 2011/0041231 | A1 | 2/2011 | Behrens et al. | 2/69 |
| 2011/0302703 | A1 | 12/2011 | Silverberg | 2/457 |
| 2012/0030851 | A1 | 2/2012 | Kinder et al. | 2/69 |
| 2012/0090072 | A1 | 4/2012 | Oprandi et al. | 2/114 |
| 2012/0291179 | A1 | 11/2012 | Shea | 2/102 |
| 2013/0205467 | A1 * | 8/2013 | Walrich | A41D 27/24 |
| | | | | 2/93 |
| 2013/0318681 | A1 * | 12/2013 | Schuh | A41D 13/0058 |
| | | | | 2/102 |
| 2015/0216242 | A1 | 8/2015 | Evans et al. | A41D 13/1245 |
| 2015/0296896 | A1 | 10/2015 | Laguna | A41C 3/0064 |
| 2015/0359269 | A1 * | 12/2015 | Rapp | A41D 27/20 |
| | | | | 2/93 |
| 2015/0366276 | A1 | 12/2015 | Kuzmanovski | A41D 13/1245 |
| 2016/0219951 | A1 | 8/2016 | Schickel | A41D 13/1236 |
| 2016/0331049 | A1 * | 11/2016 | James | A41D 13/1245 |
| 2019/0159533 | A1 * | 5/2019 | James | A41D 13/129 |

\* cited by examiner

FRONT PERSPECTIVE VIEW OF GARMENT WITH POST OPERATIVE DRAIN COMPARTMENTS

FRONT PERSPECTIVE VIEW OF OPENING OF GARMENT HAVING POST-OPERATIVE DRAIN COMPARTMENTS WHEN WORN BY USER

FRONT PERSPECTIVE VIEW OF GARMENT HAVING POST-OPERATIVE DRAIN COMPARTMENTS WHEN WORN BY USER

FRONT PERSPECTIVE VIEW OF ADOLESCENT/PEDIATRIC GARMENT WITH POST OPERATIVE DRAIN COMPARTMENTS

US 11,857,008 B1

GARMENTS FOR PEDIATRIC PATIENTS WITH POST-OPERATIVE DRAIN COMPARTMENTS

CROSS-REFERENCE TO RELATED APPLICATION

This application is a continuation-in-part of, and claims the benefit under 35 U.S.C. § 120 from, nonprovisional U.S. patent application Ser. No. 15/726,307 entitled "Garments Having Compartments That Support Post-Operative Drain Devices," filed on Oct. 5, 2017, now U.S. Pat. No. 10,188,160. The entire subject matter of the aforementioned patent document is incorporated herein by reference.

TECHNICAL FIELD

The described embodiments relate to garments, and more particularly garments that support post-operative procedures and treatment.

BACKGROUND INFORMATION

Surgical tubes and drains are often used in treating patients as part of post-operative care. Improper treatment of post-surgical areas may result in the accumulation of air or fluid, which could lead to infection of the wounded area. To prevent the undesirable accumulation of fluid, post-operative drains are typically used to remove these fluids from the surgical area. Proper use of post-operative drain usually reduces the risk of infection and tends to minimize tissue trauma. Multiple variables have an impact on the effectiveness of these drains including: the consistency of the draining fluid, the tube diameter and length, and the amount of negative pressure from the drain. Post-operative drains can be used in various types of surgeries, including abdominal, breast, and orthopedic procedures.

One common type of post-operative drain is an active drain. Active drains use a closed drainage system with low-pressure suction devices that continuously remove fluids against gravity. The active drain is attached to a collapsible reservoir that exerts negative pressure to pull accumulated fluids from the wound bed. The collection reservoir expands as it collects drainage. One example of an active post-operative drain is shown in FIG. 1 (Prior Art). A reservoir 2 is attached to a drain 3. In this example, the reservoir 2 has a bulb shape with a capacity of approximately 100.0 cubic centimeters and the drain 3 has dimensions of approximately 7.0 mm in radius and 20.0 cm in length. In another example, the shape and capacity of the reservoir 2 and drain 3 dimensions may vary based on the need. One commercially available version of the post-operative drain as shown in FIG. 1 is a Jackson-Pratt Drain (also referred to as a "JP Drain"). The drain 3 may also be referred to as a "tube" and the reservoir 2 may also be referred to as a "bulb".

One known technique is to provide one or two compartments along a garment that attaches to or is worn by a patient. The compartments may be on the outside or inside of the garment. The patient wears or attaches the garment and then inserts the post-operative drain inside the compartment. However, numerous shortcomings exist with these conventional garments. For example, many of these garments do not provide sufficient support, versatility, or ease of use that is desirable for patients that have undergone challenging medical procedures. A solution that overcomes these shortcomings is desired.

SUMMARY

A garment with post-operative drain compartments along an interior of the garment is manufactured and provided to a user. The garment is worn and used by the user after the user has undergone a surgical procedure that involves a post-operative drain. Patients that undergo certain surgeries (e.g.—Plastic, Breast, Chest, Pancreatic, Biliary, Thyroid, and Neuro) will generally result in a buildup fluid in the surgical area. After the surgery, one or more post-operative drains are attached to the person's body to help prevent the accumulation of fluid. The post-operative drain compartments of the garment support and retain the one or more post-operative drains.

Each of the post-operative drain compartments supports a reservoir of a post-operative drain. The user wears the garment and inserts the reservoir of a post-operative drain into one of the post-operative drain compartments. A tube is inserted into the operated tissue and extends to a reservoir. The reservoir is also referred to as a bulb. The garment provides a mechanism for retaining the reservoir close to the body in an inconspicuous and convenient fashion. Users need not suffer as much embarrassment of being in public, as the reservoirs are concealed from the view of others. This is one significant improvement over the prior art. Conventional techniques are undesirably limited in the number and location of accessible pockets.

The garment has a plurality of post-operative drain compartments disposed along an inner surface of a side of the garment. At least one of the plurality of post-operative drain compartments is disposed above at least another one of the plurality of post-operative drain compartments. In one example, a first post-operative drain is at least 3.0 inches above a second post-operative drain compartment. In another example, a first post-operative drain is at least 5.0 inches above a second post-operative drain compartment.

By positioning one post-operative drain compartment above another, the garment provides significant ease and versatility to the user. This is because medical procedures may involve more than one drain situated along different parts of the individual's body. For example, a first tissue opening may be positioned above a second tissue opening after a medical procedure. For user comfort, the first tissue opening is connected to a first post-operative drain that is inserted into and retained within the upper positioned post-operative drain compartment. The second tissue opening is connected to a second post-operative drain that is inserted into and retained within the lower positioned post-operative drain compartment. Thus, the novel garment provides compartments that tend to be closer to each respective tissue opening than are provided in conventionally available garments.

In one embodiment, a garment has a first plurality of post-operative drain compartments disposed on a first side, and a second plurality of post-operative drain compartments on a second side of the garment. There are at least four compartments on the first side and four compartments on the second side that mirror the compartments on the first side. At least one compartment is disposed above two or more of the other compartments on a side. The numerous locations of compartments on various levels provide the user with flexibility in selecting his or her desired reservoir placement. This gives the user the ability to use multiple compartments simultaneously. For configurations supporting multiple reservoirs, the mirrored configuration allows for appropriate weight distribution between the left and right sides of the garment.

The garment has an attachment mechanism (e.g. Velcro, buttons, zipper, or another fastening instrument) that allows the user to open and securely close then garment when needed. The attachment mechanism does not impede the drains, but rather allows the user easy access to the post-operative drain compartments when garment is opened. When the garment is closed, the post-operative drain compartments remain secure and concealed from the public eye.

One novel aspect of the garment is the orientation of the post-operative drain compartments. At least one of the post-operative drain compartments is disposed above at least two others of the post-operative drain compartments. The garment supports at least six post-operative drain compartments. The drain compartments are versatile in that they allow for many options of where to put reservoir in the garment. There are several different configurations that can fit each user's needs. The compartments are organized in a way to facilitate proper drain circulation.

In one example, each of the openings post-operative drain compartments remains open and does not include any fastening mechanism. In this configuration, there is no zipper, Velcro, buttons, or any other fastening instrument to secure the opening. In another example, each of the openings of the post-operative drain compartments include a fastening mechanism (e.g.—zipper, Velcro, buttons, or other fastening instrument). In other embodiments, the garment may be other types of clothing including, a t-shirt, a long sleeve shirt, a pajama, a vest, a zip, a coat, and a jacket.

In another embodiment, a garment having post-operative drain compartments is manufactured and provided to pediatric patients, including children and young adults. The pediatric garment has rear panel and front panel. The front panel has a right front panel and a left front panel. At least two post-operative drain compartments are disposed on either the right front panel or left front panel of the pediatric garment. A first post-operative drain compartment is disposed below a breast portion of the garment and above a waist portion. A second post-operative drain compartment is disposed below a waist portion of the garment. In some embodiments, the pediatric garment also includes an amount of fabric that extends away from the garment, such as a cape. In one example, the cape is permanently affixed to the garment. In another example, the cape is detachable from the garment, through a mechanical fastening mechanism such as Velcro, clips, or buttons. In other embodiments, one or more textual or graphical elements are affixed to an outer portion of the garment, that may include cultural figures or references, known icons, slogans, trademarks or trade names, artistic designs, or other textual or graphical elements providing visual appeal.

The novel arrangement of post-operative drain compartments provides versatility and flexibility to patients in both adult and pediatric embodiments of the novel garments. The novel arrangement of post-operative drain compartments increases mobility by not impeding movement at the waist and tends to quicken recovery by encouraging the patient to engage in public activities without the shame. In one example, the garment is formed from opaque and non-transparent material. The compartments are not visible from outside the garment. This prevents others from seeing the drains from outside the garment when the drains are disposed within the compartments.

The novel garments, including both adult and pediatric embodiments, provide at least three post-operative drain compartments on either the left front panel of the garment or on the right front panel of the garment. By placing the post-operative drain compartments sufficiently far apart, multiple drains can be accommodated without interfering with one another, potentially causing dislodgment, pain, or restriction of motion. Additionally, the post-operative drain compartments are disposed on the garments such that each front panel has one post-operative drain compartment above the waist and two or more post-operative drain compartments below the waist. The garments do not have pockets directly at the waist. This provides a significant improvement over prior art garments because the abdomen is a very common location for surgical incisions and drains placed in compartments at the waist would impede bending at the waist. In addition, no compartments are disposed on the back panel of the garment. Placing drains on the back panel would prevent the patient from comfortably and safely lying on his or her back.

Further details and embodiments and methods are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
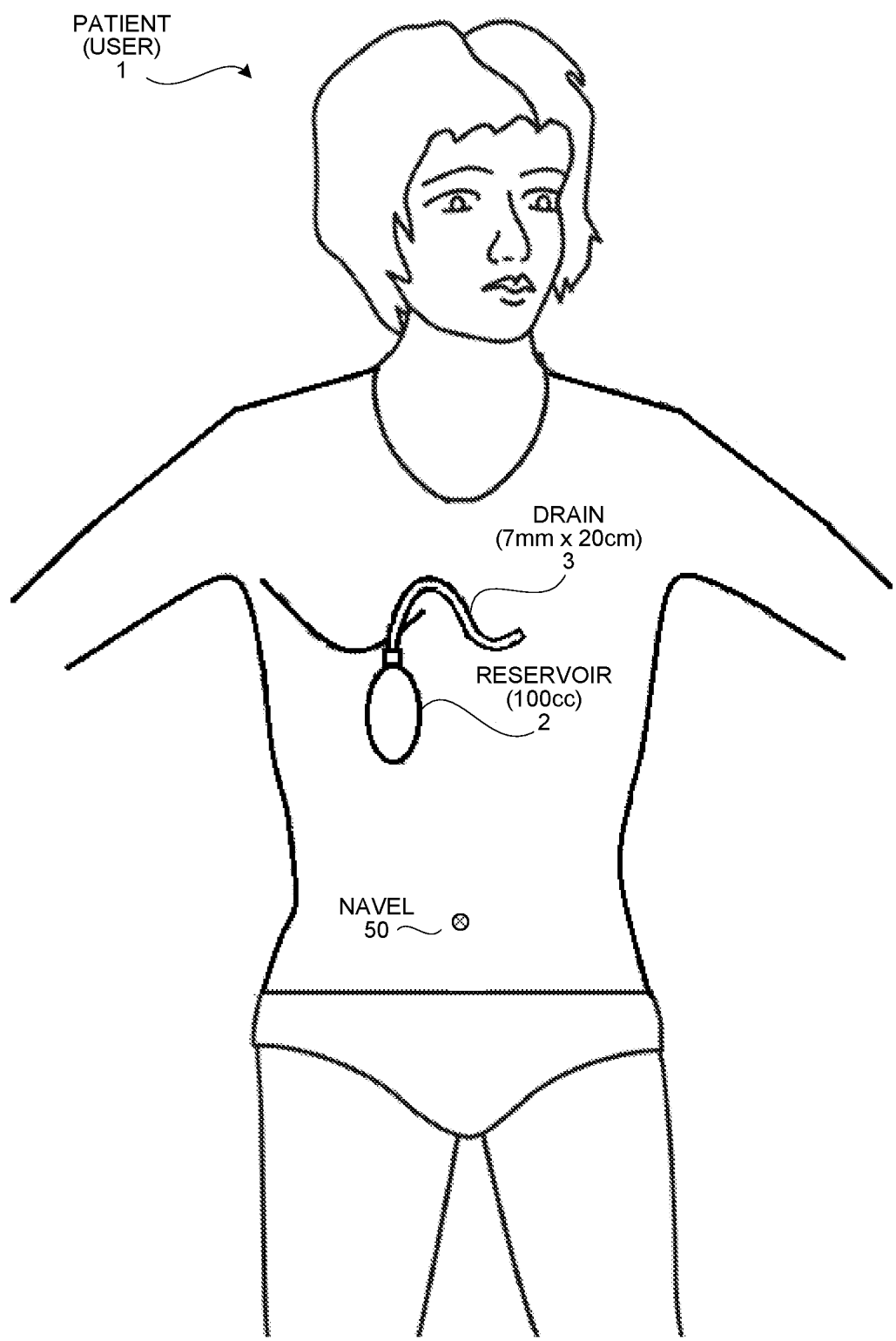
FIG. 1 (Prior Art) is a perspective diagram of a patient 1 using a post-operative drain 3 after a surgical procedure.
Figure 2:
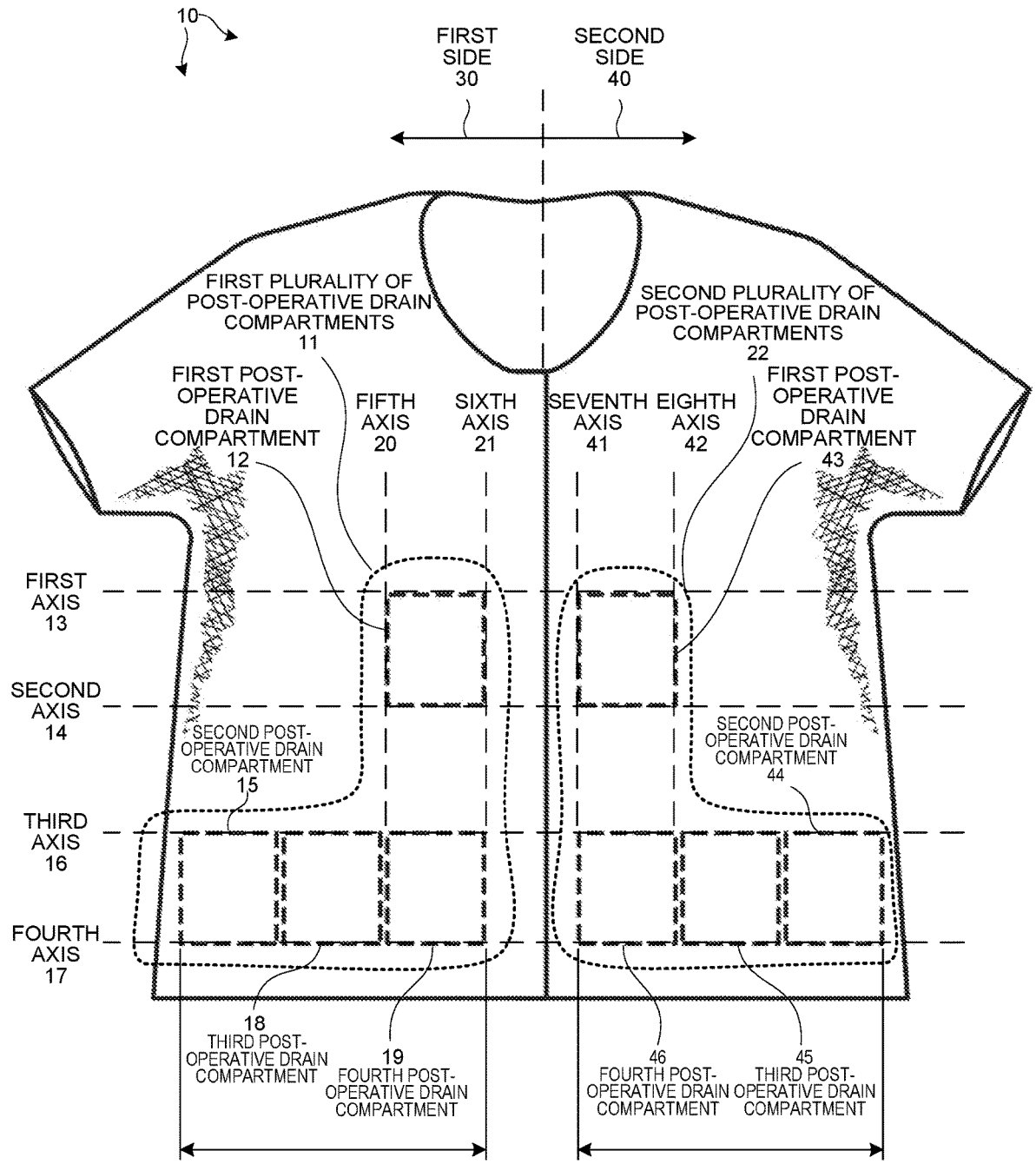
FIG. 2 is a diagram of a front perspective view of a garment 10 with post-operative drain compartments.

FIG. 2 is a diagram of a garment 10 having post-operative drain compartments. The garment 10 comprises a first side 30 and a second side 40. The first side 30 comprises a first plurality of post-operative drain compartments 11 and a second plurality of post-operative drain compartments 22. The first plurality of post-operative drain compartments 11 has a first post-operative drain compartment 12, a second post-operative drain compartment 15, a third post-operative drain compartment 18, and a fourth post-operative drain compartment 19. The second plurality of post-operative drain compartments 22 has a first post-operative drain compartment 43, a second post-operative drain compartment 44, a third post-operative drain compartment 45, and a fourth post-operative drain compartment 46.

In accordance with one novel aspect, the post-operative drain compartments are disposed along numerous axes described below. A first axis 13 is parallel to and above a second axis 14. The second axis 14 is parallel to and above a third axis 16. The third axis 16 is parallel to and above a fourth axis 17. On the first side 30, a fifth axis 20 is parallel to a sixth axis 21. On the second side 40, a seventh axis 41 is parallel to an eighth axis 42. The first, second, third, and fourth axes (13, 14, 16, 17) are perpendicular to the fifth, sixth, seventh, and eight axes (20, 21, 41, 42).

On the first side 30, the first post-operative drain compartment 12 is disposed horizontally between the first axis 13 and the second axis 14, and vertically between the fifth axis 20 and the sixth axis 21. The first post-operative drain compartment 12 is parallel to the fourth post-operative drain compartment 19. On the first side 30, the second, third, and fourth post-operative drain compartments (15, 18, 19) are disposed horizontally between the third axis 16 and the fourth axis 17. The fourth post-operative drain compartment 19 is disposed vertically between the fifth axis 20 and the sixth axis 21.

On the second side 40, the first post-operative drain compartment 43 is disposed horizontally between the first axis 13 and the second axis 14 and vertically between the seventh axis 41 and the eighth axis 42. The fourth post-operative drain compartment 46 is parallel to the first post-operative drain compartment 43. On the second side 40, the second, third, and fourth post-operative drain compartments (44, 45, 46) are disposed horizontally between the third axis 16 and the fourth axis 17. The fourth post-operative drain compartment 46 is disposed vertically between the seventh axis 41 and the eighth axis 42. By orienting the post-operative drain compartments in this way, the user of the garment is given significant versatility in securing post-operative drains.

Figure 3:
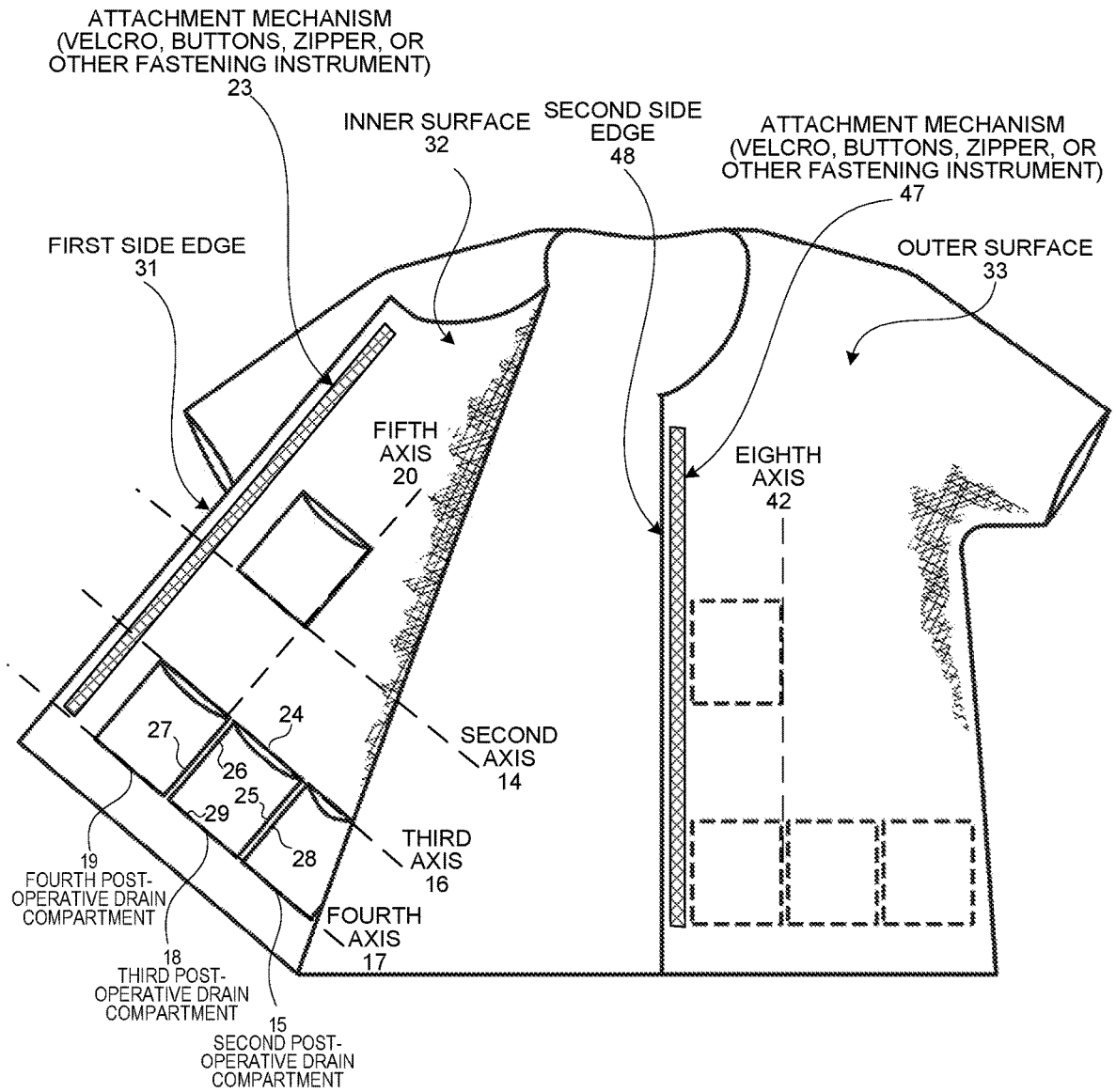
FIG. 3 is a diagram showing an inner surface 32 of the garment 10 having the post-operative drain compartments.

FIG. 3 is a diagram of an opening of a garment 10 having post-operative drain compartments. In this example, the third post-operative drain compartment 18 has four edges. A first edge 24 is disposed along the third axis 16. A second edge 25 is disposed along a fourth edge of the second post-operative drain compartment 28. A third edge 29 is disposed along the fourth axis 17. The fourth edge 26 is disposed along a second edge of the fourth post-operative drain compartment 27. In one example, the garment 10 is manufactured using natural fibers. In another example, the garment 10 is manufactured using synthetic fibers. In yet another example, the garment 10 is manufactured using a combination of natural fibers and synthetic fibers. In one example, the garment 10 comprises a material selected from the group consisting of: cotton, flax, wool, ramie, silk, denim, leather, down, fur, nylon, and polyester.

On an inner surface 32 of the first side 30, an attachment mechanism 23, for example, Velcro, buttons, zipper, or other fastening instrument, is along a first side edge 31 and parallel to the fifth axis 20. On the outer surface 33 of the second side 40, another attachment mechanism 47 that complements the attachment mechanism 23, for example, Velcro, buttons, zipper, or other fastening instrument, is along a second side edge 48 and parallel to the eighth axis 42.

Figure 4:
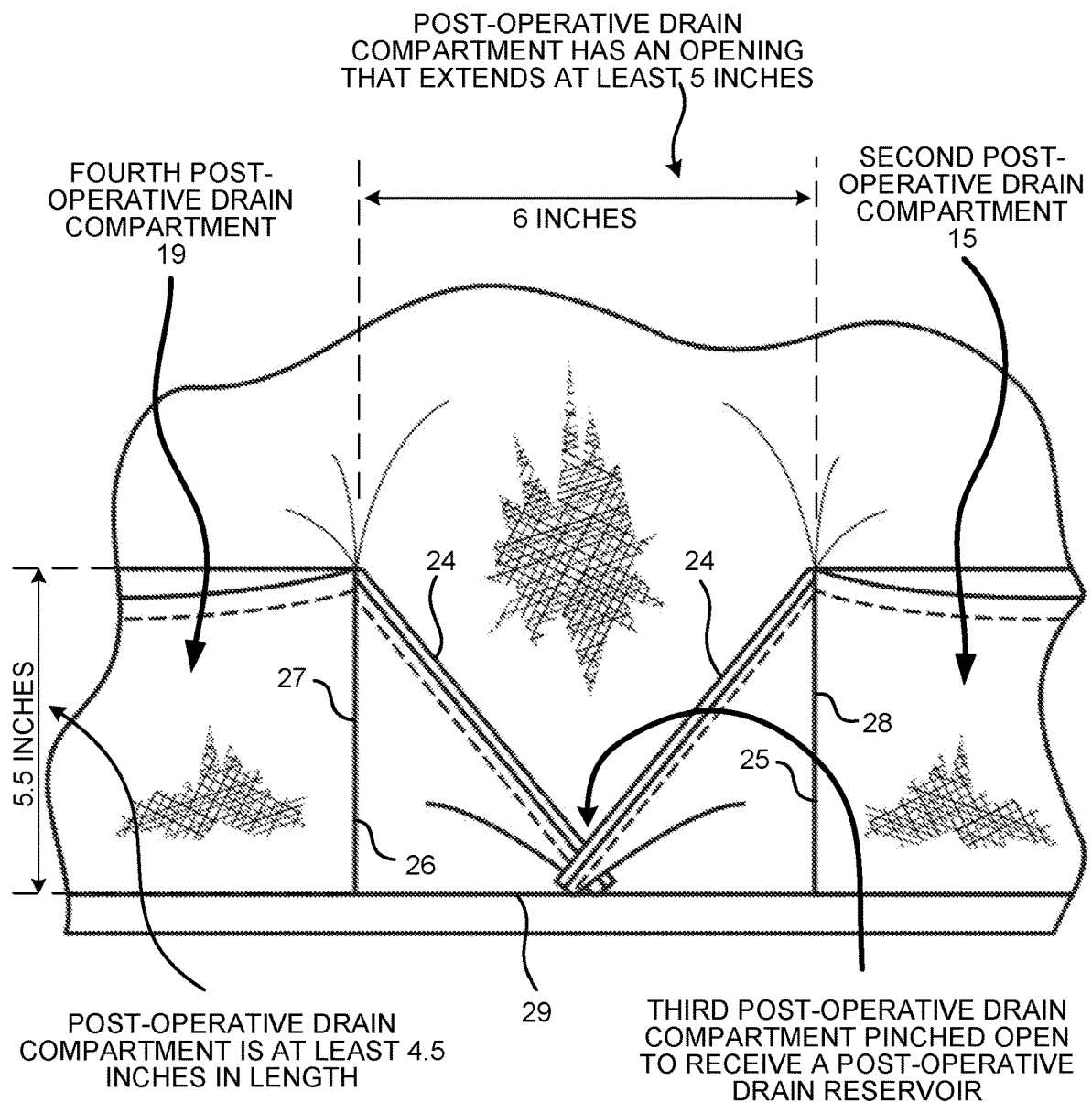
FIG. 4 is a diagram showing how one of the post-operative drain compartments is pinched open to receive a post-operative drain reservoir.

FIG. 4 is a diagram of a post-operative drain compartment pinched open to receive a post-operative drain. The first edge (or upper extent) of each of the plurality of the post-operative drain compartments has an opening that extends at least 5 inches. The second and fourth edges (or side edges) of each of the plurality of the post-operative drain compartments extend at least 4.5 inches. These dimensions provide optimal retaining volume for reservoirs of typical post-operative drains. In this example, the first edge extends approximately 6.0 inches and the side edges extend approximately 5.5 inches.

In this example, each of the bottom and side edges of the post-operative drain compartment is stitched into the inner surface 32 of the garment 10. In another example, the post-operative drain compartments are glued onto the inner surface 32 of the garment 10. In another example, the post-operative drain compartments are attached to the inner surface 32 of the garment 10 using another attachment mechanism such as a safety pin, magnet, buttons, zippers, Velcro, or a combination of the above.

In accordance with another novel aspect, the upper edge of each post-operative drain compartment remains open thereby providing easy and quick storage of the post-operative drains. In the example of FIG. 4, the first edge of the third post-operative drain compartment 24 is shown pinched open to receive a post-operative drain. In one example, none of the post-operative drains has a closure mechanism or fastening mechanism that securely shuts the opening provided by the first edge (or upper edge). In the example of FIG. 4, the post-operative drains do not have any zipper, button, Velcro, or similar fastening mechanism and always remain open to provide ease of access. In another example, the post-operative drains have a closure mechanism or fastening mechanism that securely shuts the opening provided by the first edge (or upper edge), such as a zipper, button, Velcro, or similar fastening mechanism.

Figure 5:
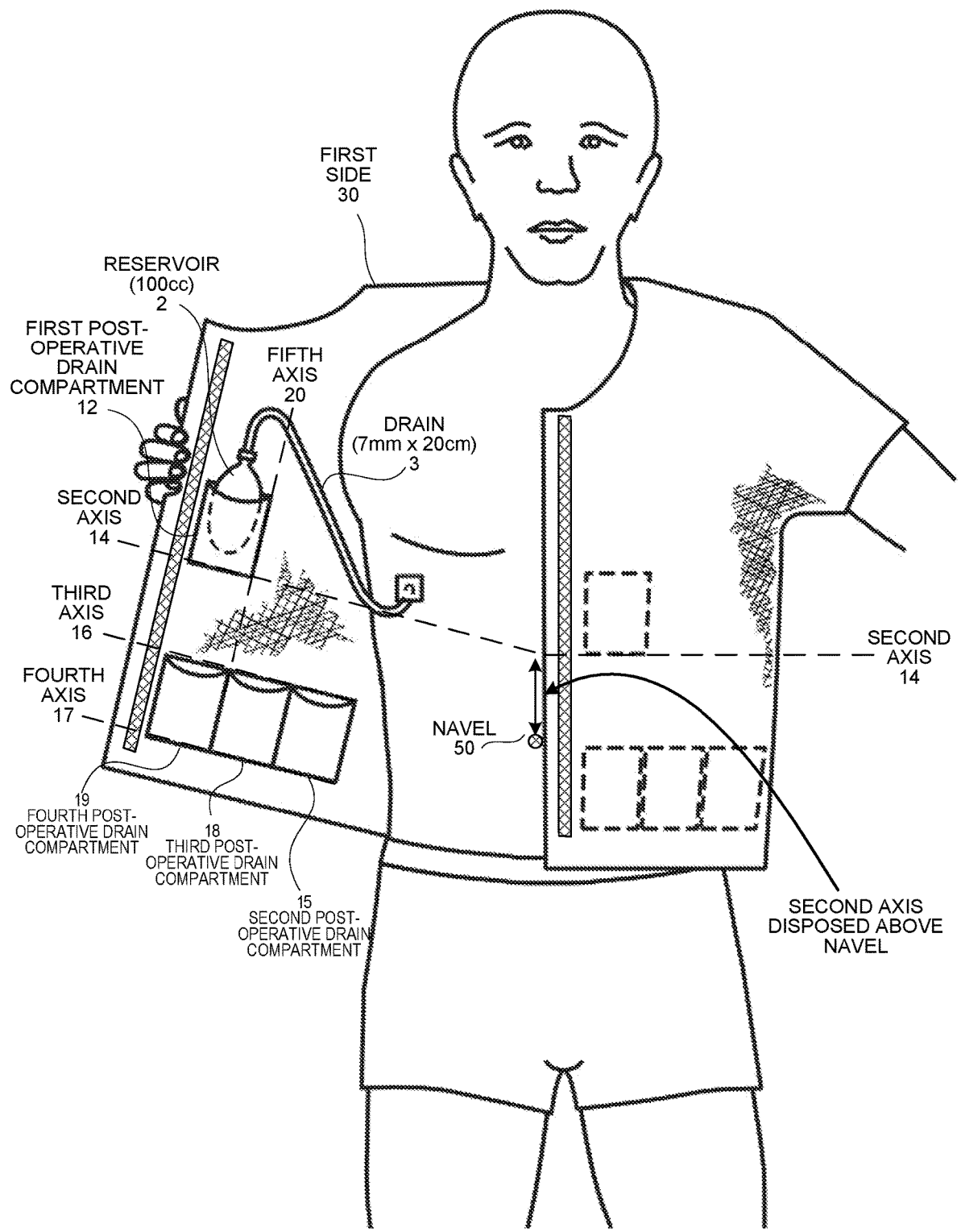
FIG. 5 is a diagram of a front perspective view of opening of a garment having post-operative drain compartments when worn by user.

FIG. 5 is a diagram of the front perspective view of the garment having post-operative drain compartments 10 when worn and opened. The second axis 14 is disposed above the navel 50. At least one post-operative drain compartment is disposed above the navel 50 when worn by the user and the at least one post-operative drain compartment is also disposed above another post-operative drain compartment that is disposed below the navel 50. In this example, the first post-operative drain compartment 12 is in use. In another example, other post-operative drain compartments may be used to support post-operative drains.

Figure 6:
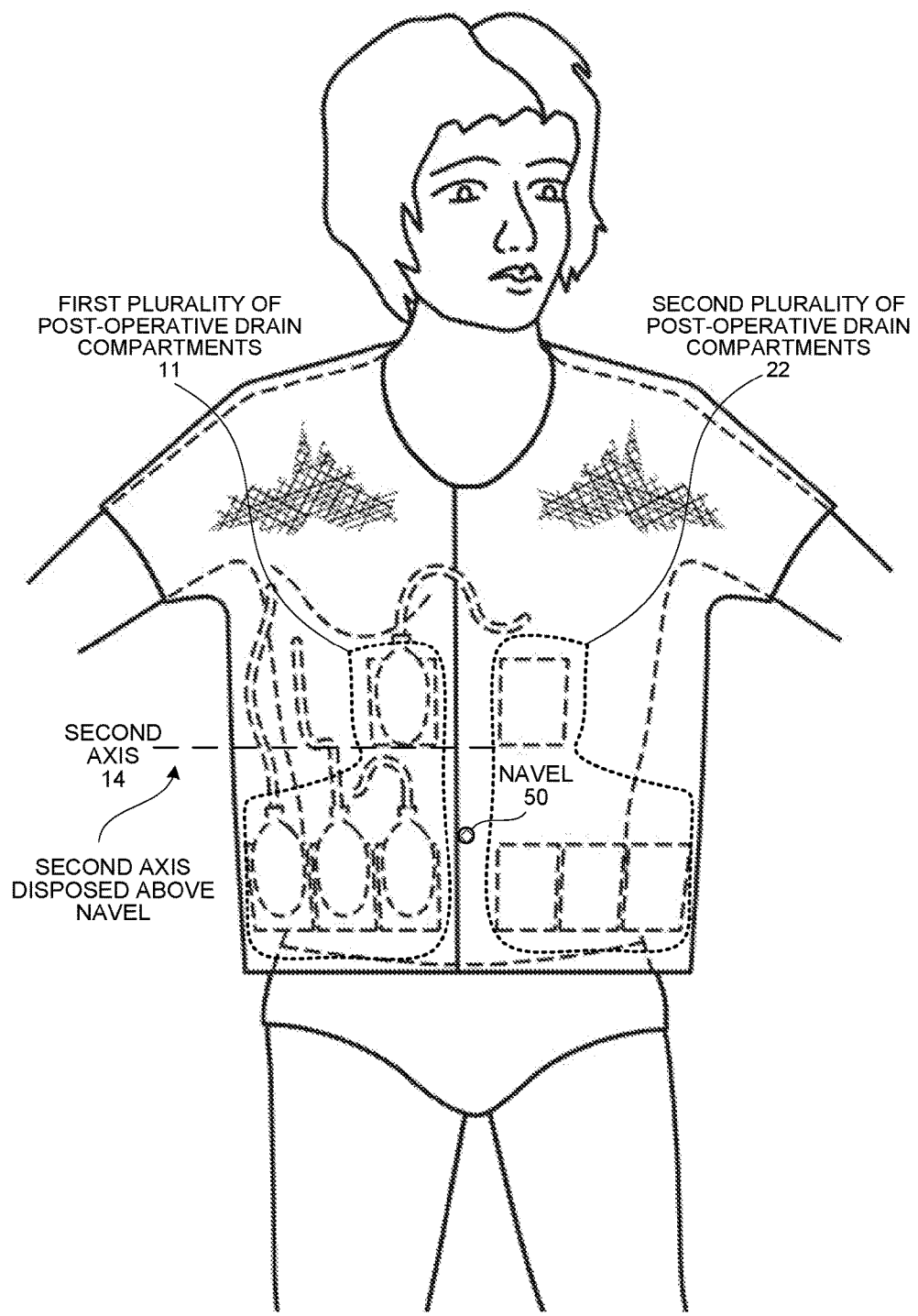
FIG. 6 is a diagram of a front perspective view of a garment having post-operative drain compartments when worn by user.

FIG. 6 is a diagram of the front perspective view of the garment having post-operative drain compartments 10 when worn and closed. The second axis 14 is disposed above the navel 50. In this example, each post-operative drain compartment in the first plurality 11 is in use. In another example, the second plurality of post-operative drain compartments 22 may be in use.

Figure 7:
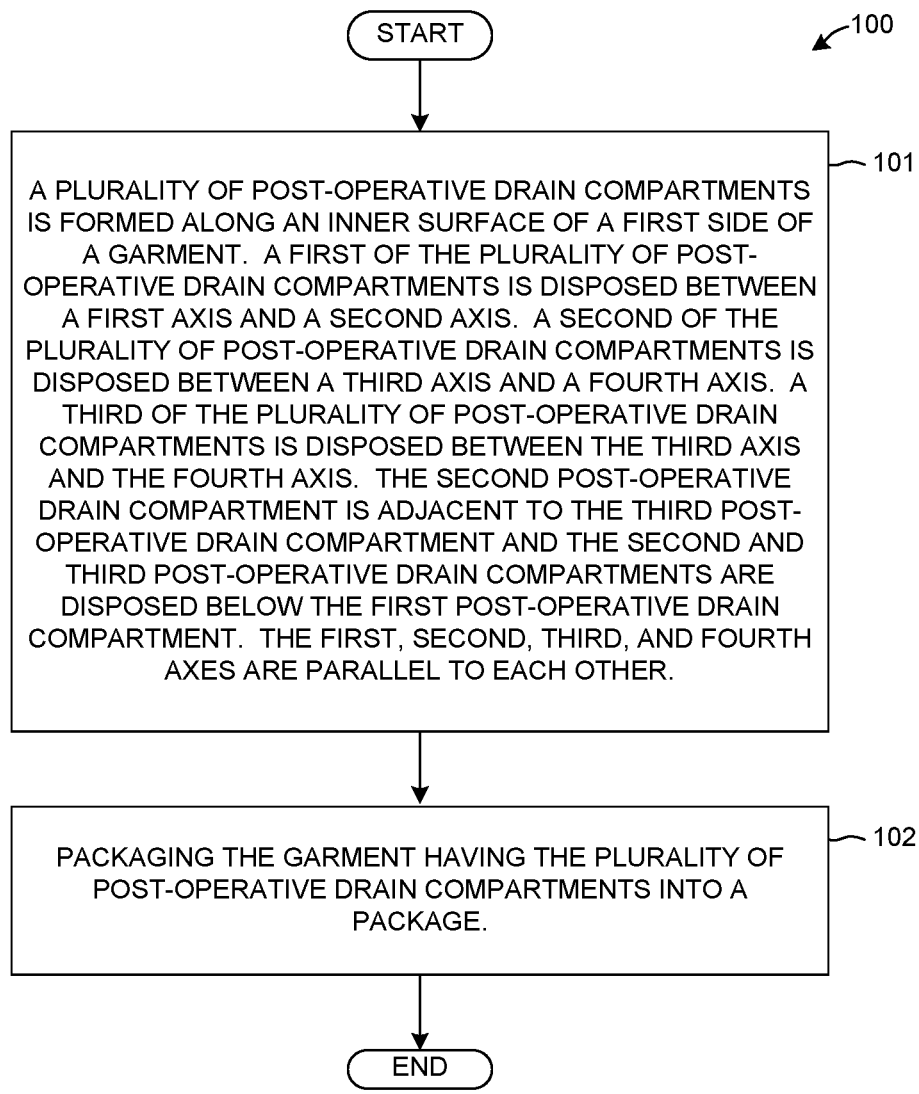
FIG. 7 is a flowchart of a method 100 in accordance with one novel aspect.

FIG. 7 is a flowchart of a method 100 in accordance with one novel aspect. In a first step (step 101), a plurality of post-operative drain compartments is formed along an inner surface 32 of a first side of a garment. A first of the plurality of post-operative drain compartments is disposed between a first axis and a second axis. A second of the plurality of post-operative drain compartments is disposed between a third axis and a fourth axis. A third of the plurality of post-operative drain compartments is disposed between the third axis and the fourth axis. The second post-operative drain compartment is adjacent to the third post-operative drain compartment and the second and third post-operative drain compartments are disposed below the first post-operative drain compartment. The first, second, third, and fourth axes are parallel to each other. For example, in FIG. 2, the garment 10 has a first plurality of post-operative drain compartments 11 formed along the inner surface 32 of the first side 30. There are a first, second, third, and fourth post-operative drain compartments (12, 15, 18, 19) on the first side 30. In the example of FIG. 5, a reservoir (100 cc) 2 occupying the first post-operative drain compartment 12. The reservoir 2 is connected to a drain (7 mm×20 cm) 3. In another example, there may be a reservoir of a post-operative drain occupying each post-operative drain compartment.

Figure 8:
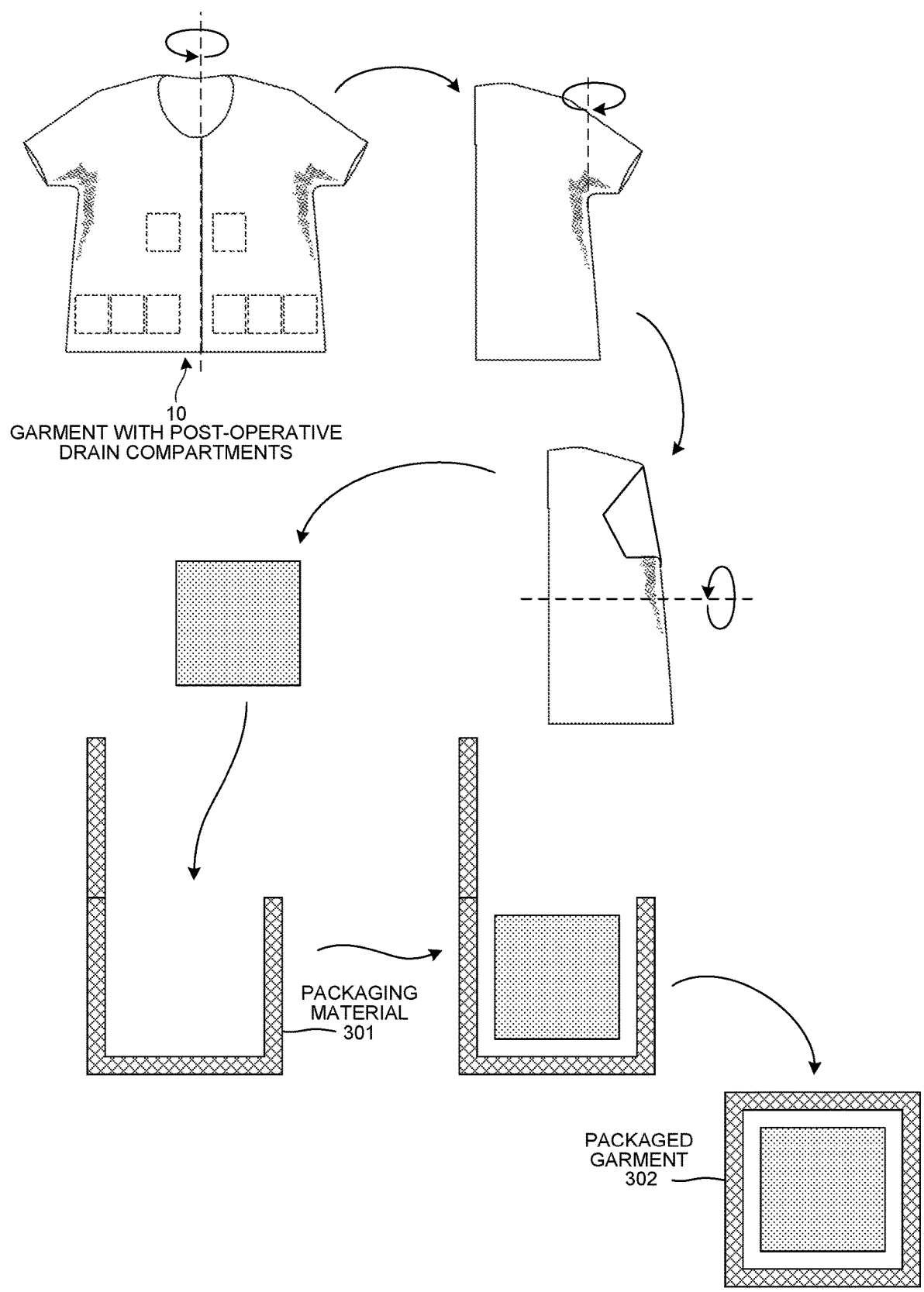
FIG. 8 is a diagram showing how to package a garment having post-operative drain compartments.

In second step (step 102), the garment with post-operative drain compartments is packed using packaging material. In the example in FIG. 8, the garment 10 is folded compactly and packaged into the packaging material 301. The packaged garment 302 is then distributed to medical retailers or other sales distribution channels.

Figure 9:
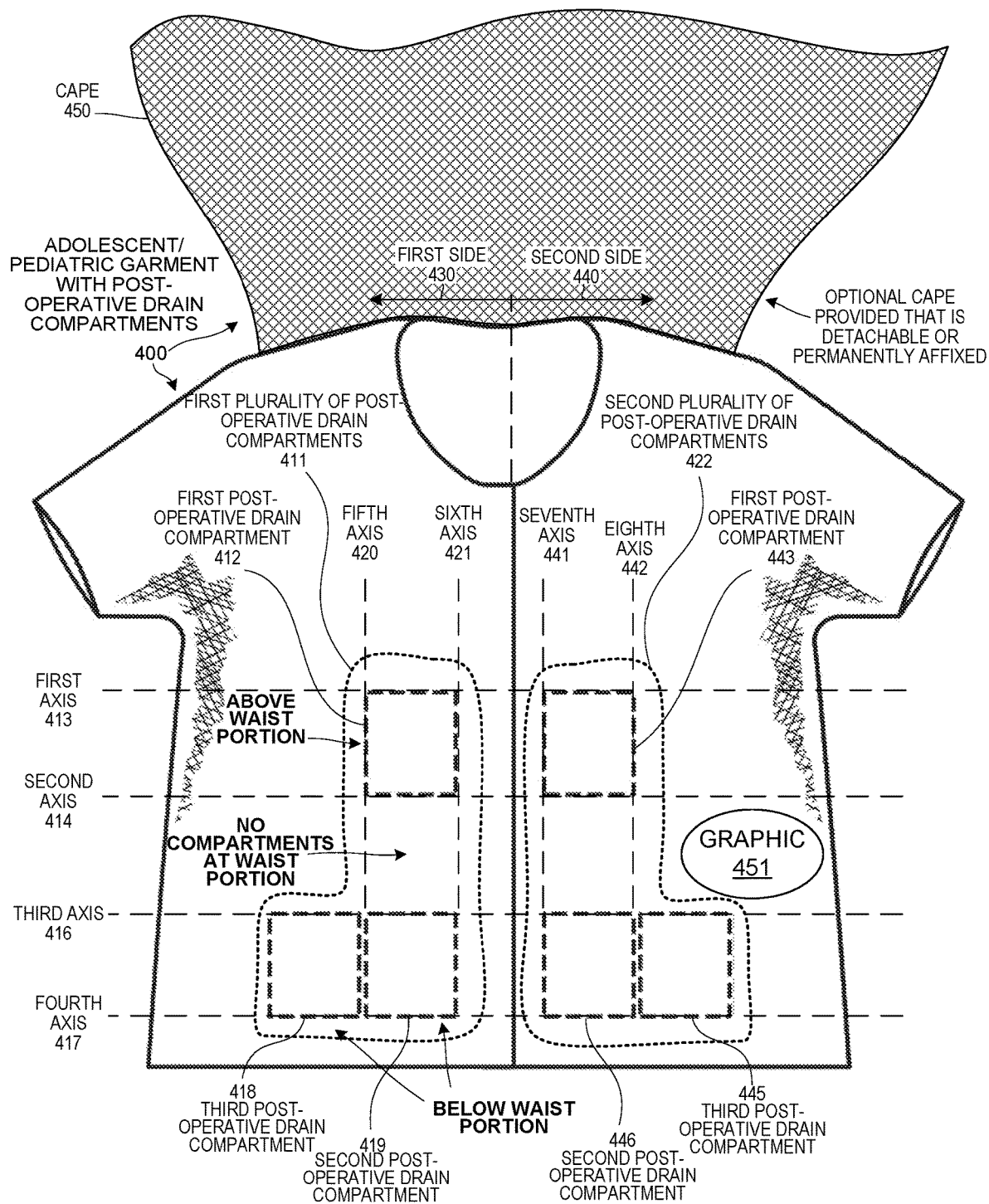
FIG. 9 is a diagram of a garment 400 having post-operative drain compartments for pediatric patients.

FIG. 9 is a diagram of a garment 400 having post-operative drain compartments for pediatric patients. The garment 400 is manufactured and provided to pediatric patients, including children and young adults. The garment 400 has at least one less compartment post-operative drain on each side than garment 10. The garment 400 has smaller dimensions than the garment 10 of FIG. 2. In one example, the garment 400 has drain compartments that are one-inch smaller in at least one-dimension as compared to drain compartments of garment 10. In another example, the garment 400 has drain compartments that are the same dimensions as compared to drain compartments of garment 10.

The garment 400 comprises a first side 430 and a second side 440. The first side 430 comprises a first plurality of post-operative drain compartments 411 and a second plurality of post-operative drain compartments 422. The first plurality of post-operative drain compartments 411 has a first post-operative drain compartment 412, a second post-operative drain compartment 419, and a third post-operative drain compartment 418. The second plurality of post-operative drain compartments 422 has a first post-operative drain compartment 443, a second post-operative drain compartment 446, and a third post-operative drain compartment 445.

In accordance with one novel aspect, the post-operative drain compartments are disposed along numerous axes described below. A first axis 413 is parallel to and above a second axis 414. The second axis 414 is parallel to and above a third axis 416. The third axis 416 is parallel to and above a fourth axis 417. On the first side 430, a fifth axis 420 is parallel to a sixth axis 421. On the second side 440, a seventh axis 441 is parallel to an eighth axis 442. The first, second, third, and fourth axes (413, 414, 416, 417) are perpendicular to the fifth, sixth, seventh, and eight axes (420, 421, 441, 442).

On the first side 430, the first post-operative drain compartment 412 is disposed horizontally between the first axis 413 and the second axis 414, and vertically between the fifth axis 420 and the sixth axis 421. The first post-operative drain compartment 412 is parallel to the second post-operative drain compartment 419. On the first side 430, the second and third post-operative drain compartments (418 and 419) are disposed horizontally between the third axis 416 and the fourth axis 417. The second post-operative drain compartment 19 is disposed vertically between the fifth axis 420 and the sixth axis 421. Although the second post-operative drain compartment 419 is shown disposed directly below the first post-operative drain compartment 412, in other embodiments the second post-operative drain compartment 419 is offset to the left or right and not directly below the first post-operative drain compartment 412.

On the second side 440, the first post-operative drain compartment 443 is disposed horizontally between the first axis 413 and the second axis 414 and vertically between the seventh axis 441 and the eighth axis 442. The second post-operative drain compartment 446 is parallel to the first post-operative drain compartment 443. On the second side 440, the second and third (445 and 446) are disposed horizontally between the third axis 416 and the fourth axis 417. The second post-operative drain compartment 446 is disposed vertically between the seventh axis 441 and the eighth axis 442. By orienting the post-operative drain compartments in this way, the user of the garment is given significant versatility in securing post-operative drains. Although the second post-operative drain compartment 446 is shown disposed directly below the first post-operative drain compartment 443, in other embodiments the second post-operative drain compartment 446 is offset to the left or right and not directly below the first post-operative drain compartment 443.

In accordance with another novel aspect, an amount of fabric 450 is attached to the garment 400 and extends away from the garment. In one example, the amount of fabric 450 is a cape. The cape 450 is permanently affixed to the garment 400 or is detachable via Velcro, buttons, clips, or other types of mechanical fastening mechanisms. The cape 450 adds significant appeal to adolescent or pediatric users. The cape 450 is provided to mimic that of a super hero or action hero. In other embodiments, the garment 400 is provided without any cape 450.

In accordance with yet another novel aspect, one or more textual or graphical elements 451 are affixed to an outer portion of the garment. The textual or graphical elements 451 add additional appeal to children and adolescent users of garment 400. The textual or graphical elements 451 may include cultural figures or references, known icons, slogans, trademarks or trade names, artistic designs, or similar text or graphical elements. In other embodiments, the garment 400 is provided without any added textual or graphical elements 451.

Although certain specific exemplary embodiments are described above in order to illustrate the invention, the invention is not limited to the specific embodiments. For example, although the garment is shown as a t-shirt, in other embodiments, the garment may be a long sleeve shirt, a pajama, a vest, a zip, a coat, and a jacket. The example of FIG. 2 has a set of compartments on each side, however, in other embodiments, the compartments are all disposed along a single side. Although the compartments of FIG. 2 have one compartment above three lower compartments, in another example, the compartments have two upper compartments that are aligned between first and second axes 13,14 and two lower compartments that are aligned between the third and fourth axes 16,17. In yet another example, there are compartments situated vertically between two other compartments. For example, one compartment is disposed above a second compartment, which in turn, is disposed above a third compartment. The first, second and third compartments are stacked vertically. In another embodiment, the compartments are disposed along a grid pattern such that a compartment is selectively disposed at along elements of the grid pattern. The grid has dimensions A×B taken from group consisting of: 1×1, 1×2, 1×3, 1×4, 2×1, 2×2, 2×3, 3×4, 3×1, 3×2, 3×3, 3×4, and 4×1, 4×2, 4×3, and 4×4. The dimension "A" represents the number of compartments horizontally along the grid (for example, parallel to the first axis 13) and the dimension "B" represents the number of compartments vertically along the grid (for example, parallel to the fifth axis 20). One or more of grids may selectively not have any compartment to provide a gap between the compartments. Accordingly, various modifications, adaptations, and combinations of various features of the described embodiments can be practiced without departing from the scope of the invention as set forth in the claims.

What is claimed is:

1. A garment comprising:
   an inner surface;
   an outer surface;
   a front panel comprising a left front panel and a right front panel;
   a rear panel;
   a waist portion;
   a first post-operative drain compartment having a height and width disposed along the inner surface of the front panel of the garment, wherein an upper edge of the first post-operative drain compartment provides a first opening along the width, wherein the first post-operative drain compartment is disposed above the waist portion and wherein the first post-operative drain compartment is disposed below a breast portion of the garment;
   a second post-operative drain compartment disposed along the inner surface of the front panel of the garment, wherein the second post-operative drain compartment has the height and width, an upper edge, two opposing side edges and a lower edge, wherein the upper edge of the second post-operative drain compartment provides a second opening along the width, wherein a distance between the upper edge of the second post-operative drain compartment and a lower edge of the first post-operative drain compartment is substantially equal to the height and defines the waist portion, wherein the second post-operative drain compartment is disposed below the waist portion; and
   a third post-operative drain compartment disposed along the inner surface of the front panel of the garment, the third post-operative drain compartment having the height and width, a second upper edge positioned along a same axis as the upper edge, two second opposing side edges and a second lower edge wherein the second post-operative drain compartment adjoins with the third post-operative drain compartment along one of the two opposing side edges and one of the second opposing side edges, wherein the second and third post-operative drain compartments are disposed below the first post-operative drain compartment, and wherein the first, second, and third post-operative drain compartments are all disposed only on the front panels and there are no drain compartments located at the waist portion.

2. The garment of claim 1, wherein each of the post-operative drain compartments has a rectangular shape, wherein each of the post-operative drain compartments is of a substantially same size, and wherein no compartments contact the waist portion of the garment.

3. The garment of claim 1, wherein the garment is selected from the group consisting of: a post-operative drain garment adapted to be worn by a child, and an adolescent post-operative drain garment adapted to be worn by an adolescent.

4. The garment of claim 1, wherein the garment includes a cape that extends away from the garment.

5. The garment of claim 1, wherein the first post-operative drain compartment has an opening that extends at least four inches, and wherein the first post-operative drain compartment does not include any fastening mechanism thereby providing constant access to an interior of the first post-operative drain compartment.

6. The garment of claim 1, further comprising:
   a fourth post-operative drain compartment disposed along the inner surface of the garment;
   a fifth post-operative drain compartment disposed along the inner surface of the garment; and
   a sixth post-operative drain compartment disposed along the inner surface of the garment.

7. The garment of claim 6, wherein the first, second, and third post-operative drain compartments are disposed on one of either the left front panel or the right front panel and the fourth, fifth, and sixth post-operative drain compartments are disposed on an other of either the left front panel or the right front panel.

8. The garment of claim 1, wherein the garment has no more than four post-operative drain compartments on the left front panel, and wherein the garment has no more than four post-operative drain compartments on the right front panel.

9. The garment of claim 1, wherein the second and third post-operative drain compartments are disposed along a lower edge of the garment.

10. The garment of claim 1, wherein the distance between the upper edge of the second post-operative drain compartment and the lower edge of the first post-operative drain compartment is at least three inches.

11. The garment of claim 1, wherein the upper edge of the second post-operative drain compartment is parallel to the upper edge of the first post-operative drain compartment, and wherein the lower edge of the second post-operative drain compartment is parallel to the upper edge of the first post-operative drain compartment.

* * * * *